(12) United States Patent
Zinser, Jr. et al.

(10) Patent No.: US 7,471,977 B2
(45) Date of Patent: Dec. 30, 2008

(54) METHOD AND SYSTEM FOR DETECTING PACE PULSES

(75) Inventors: Richard Louis Zinser, Jr., Niskayuna, NY (US); Emad Andarawis Andarawis, Ballston Lake, NY (US); Jeffrey Michael Ashe, Gloversville, NY (US); Nicholas George Richard, Lakeville, MA (US)

(73) Assignee: General Electric Company, Niskayuna, NY (US)

( * ) Notice: Subject to any disclaimer, the term of this patent is extended or adjusted under 35 U.S.C. 154(b) by 542 days.

(21) Appl. No.: 10/881,865

(22) Filed: Jun. 30, 2004

(65) Prior Publication Data

US 2006/0020219 A1 Jan. 26, 2006

(51) Int. Cl.
*A61B 5/04* (2006.01)
(52) U.S. Cl. ..................................... 600/509
(58) Field of Classification Search ............... None
See application file for complete search history.

(56) References Cited

U.S. PATENT DOCUMENTS

| | | | | |
|---|---|---|---|---|
| 4,170,227 A * | 10/1979 | Feldman et al. | ............. | 600/517 |
| 4,781,200 A * | 11/1988 | Baker | ......................... | 600/483 |
| 4,832,041 A * | 5/1989 | Wang et al. | ................ | 600/510 |
| 5,088,491 A * | 2/1992 | Schaldach | ..................... | 607/18 |
| 5,448,997 A * | 9/1995 | Kruse et al. | ................. | 600/510 |
| 5,682,902 A * | 11/1997 | Herleikson | ................... | 600/521 |
| 5,683,425 A * | 11/1997 | Hauptmann | .................. | 607/9 |
| 5,913,828 A * | 6/1999 | Russell | ....................... | 600/509 |
| 5,951,483 A * | 9/1999 | Joo | ............................. | 600/509 |
| 5,961,468 A * | 10/1999 | Emmrich | ..................... | 600/510 |
| 6,163,724 A * | 12/2000 | Hemming et al. | ............. | 607/28 |
| 6,477,404 B1 * | 11/2002 | Yonce et al. | ................. | 600/510 |
| 6,920,350 B2 * | 7/2005 | Xue et al. | ..................... | 600/523 |

OTHER PUBLICATIONS

Timo Lensu, Markku Vehviläinen, Hannu Tenhunen Yrjö Neuvo; "Detection of Rectangular Pulses Using Median Based Prefiltering";CH2872-0/90/0000-0224 1990IEEE; pp. 224-227.

* cited by examiner

*Primary Examiner*—Carl H. Layno
*Assistant Examiner*—Jon-Eric Morales
(74) *Attorney, Agent, or Firm*—Fletcher Yoder

(57) ABSTRACT

The present technique provides for the detection of pace pulses in electrocardiogram data. The technique provides for processing one or more sets of electrocardiogram data via a non-linear algorithm. Furthermore, the technique provides for detecting one or more pace pulses in the one or more sets of electrocardiogram data via a non-linear detection algorithm. Systems and computer programs that afford functionality of the type defined by this method are also provided by the present technique.

75 Claims, 3 Drawing Sheets

METHOD AND SYSTEM FOR DETECTING PACE PULSES

BACKGROUND

The invention relates generally to an electrocardiogram system, and more specifically to the enhanced detection of pace pulses in electrocardiogram data.

A pacemaker is an electronic device used to treat patients who have symptoms caused by abnormally slow heartbeats. The pacemaker keeps track of the patient's heartbeat. For instance, if the patient's heart is beating too slowly, the pacemaker may generate electrical signals similar to that of the heart's natural signals, thereby causing the heart to beat faster. The purpose of the pacemaker is to maintain heartbeats in order to ensure that adequate oxygen and nutrients are delivered through the blood to the organs of the body.

Furthermore, an electrocardiogram (ECG or EKG) is generally, though not always, a non-invasive technique used to reflect underlying heart conditions by measuring the electrical activity of the heart. By positioning leads on or in the body in standardized locations, information about many heart conditions may be learned by looking for characteristic patterns in the ECG.

In order to efficiently evaluate ECG results, the diagnostician must know if the heart is being actively paced. However, due to rapid advancement in technology, the modern pacemakers are increasingly using lower voltages and power levels than those previously employed. Hence, the output from these newer pacemakers is often not visible on a conventional ECG machine.

It is becoming increasingly difficult to efficiently detect pace pulses in an adverse clinical ECG environment. Furthermore, the detection of pace pulses may be complicated by the presence of spurious signals such as impulsive noise and programmer pulses. It may be desirable to develop a robust technique to detect pace pulses in raw ECG data.

BRIEF DESCRIPTION

Briefly, in accordance with an exemplary embodiment of the present technique, a method for detecting pace pulses is presented. The method includes processing one or more sets of electrocardiogram data via a non-linear algorithm. Furthermore, the method includes detecting one or more pace pulses in the one or more sets of electrocardiogram data via a non-linear detection algorithm. Systems and computer programs that afford functionality of the type defined by this method are also provided by the present technique.

According to a further embodiment of the present invention, a method for detecting pace pulses is presented. The method includes processing one or more sets of electrocardiogram data with a differentiator. Additionally, the method includes applying a non-linear pulse signature enhancement to the one or more sets of electrocardiogram data. Systems and computer programs that afford functionality of the type defined by this method are also provided by the present technique.

In accordance with another embodiment of the present technique, a method for detecting a pace pulse is presented. The method includes detecting a signal to noise ratio. In addition, the method includes detecting the pace pulse based upon the signal to noise. Systems and computer programs that afford functionality of the type defined by this method are also provided by the present technique.

In accordance with an exemplary embodiment of the present invention, a method for combining two or more sets of electrocardiogram data is presented. The method includes combining the two or more sets of electrocardiogram data via a cross-multiplicative combiner to generate a single combined set of electrocardiogram data. Systems and computer programs that afford functionality of the type defined by this method are also provided by the present technique.

DRAWINGS

DETAILED DESCRIPTION

Modern pacemakers are increasingly employing significantly lower voltages and power levels than those previously employed. Consequently, the output from these new pacemakers may not be visible in electrocardiogram data using existing techniques. It may therefore be desirable to develop techniques that enable the efficient detection of these high-bandwidth, low-power pace pulses in electrocardiogram data so that a diagnostician may be made aware that a heart is being actively paced. The techniques discussed herein address some or all of these issues.

Figure 1:
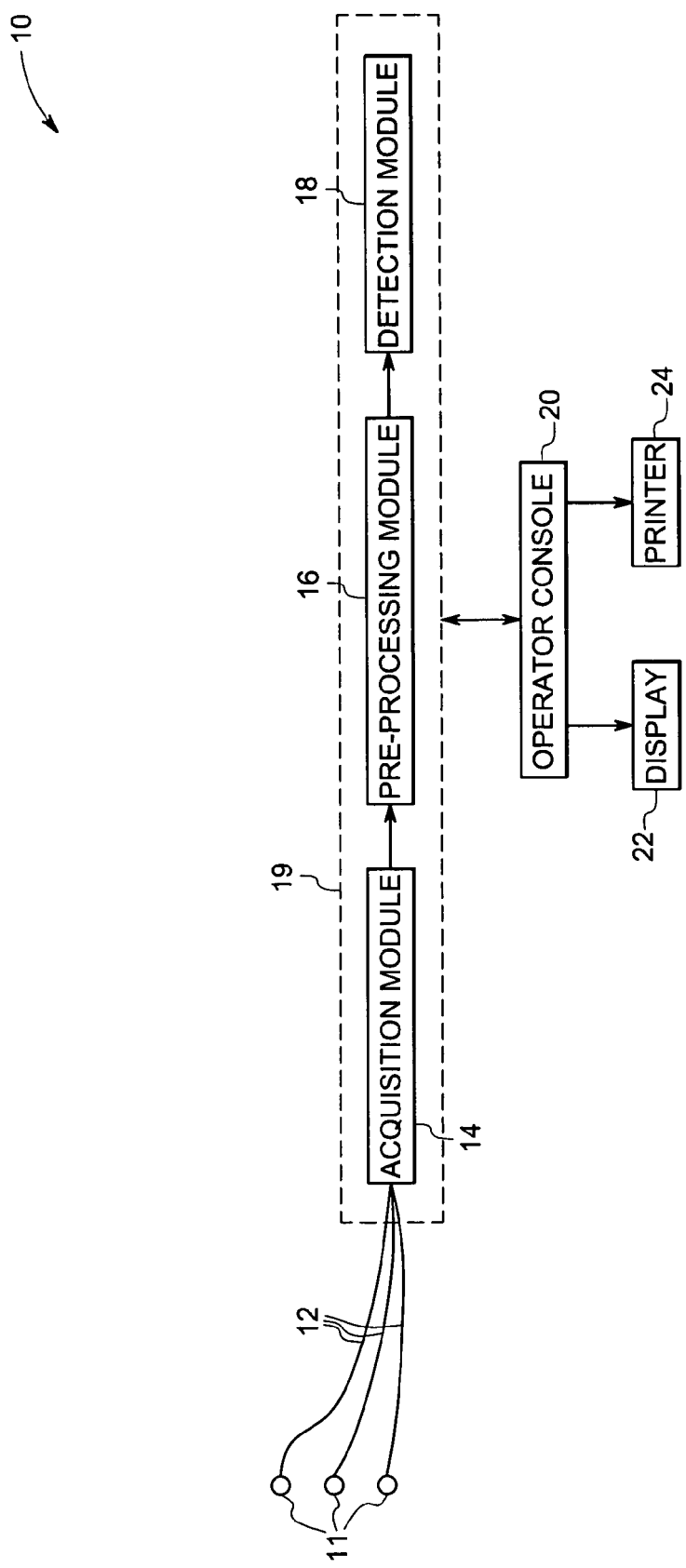
FIG. 1 is a block diagram of a system for detecting pace pulses in electrocardiogram data.

Referring to FIG. 1, a block diagram depicting an electrocardiogram (ECG) system 10 that detects pace pulses in accordance with the present technique is illustrated. The ECG system 10 may include a plurality of electrodes 11 configured to be disposed on or in a patient. Also, as shown as in FIG. 1, a plurality of electrode wires 12 facilitates the acquisition of ECG data from the electrodes 11 by an acquisition module 14. While wires 12 may be used in some exemplary implementations, other exemplary implementations may use wireless techniques, such as infrared or radio frequency transmission, for providing ECG data from the electrodes 11 to the acquisition module 14. In addition, while electrodes 11 and wires 12 may be used to directly acquire ECG data from a patient, the acquisition module 14 may instead acquire stored ECG data from an archive site or data storage facility. The acquisition module 14 may include circuitry to digitize the ECG data, if needed, or such digitization may occur in another downstream module.

The ECG system 10 may include a pre-processing module 16 that may be configured to process the ECG data acquired by the acquisition module 14. The pre-processing module 16 may facilitate processing the ECG data prior to the detection of pace pulses, where the processing may include steps such as, but not limited to, filtering, differentiating, and applying a non-linear pulse signature enhancement. For example, the pre-processing module 16 may process the ECG data by filtering the acquired sets of ECG data, as described herein. Similarly, the pre-processing module may include general or specialized circuitry for differentiating the separate ECG signals, for applying enhancement algorithms, and/or for combining separate ECG signals into a single ECG signal. The enhancement algorithms may employ non-linear processing techniques, where non-linearity may be defined by violation of the superposition principle, or by distortion of the signal such that the output signal amplitude does not scale linearly with the input amplitude.

Furthermore, the ECG system 10 may include a detection module 18 that may be configured to detect pace pulses in the ECG data. The various modules and processing components, such as acquisition module 14, pre-processing module 16 and the detection module 18 may constitute an acquisition and detection system 19 that may be accessed and/or operated via an operator console 20. The operator console 20 may also be employed to facilitate the display of detected pace pulses, such as on a display 22 and/or a printer 24. For example, an operator may use the operator console 20 to designate the manner in which detected pace pulses are displayed, such as on a separate trace from the corresponding ECG data or superimposed on the corresponding ECG data.

Figure 2:
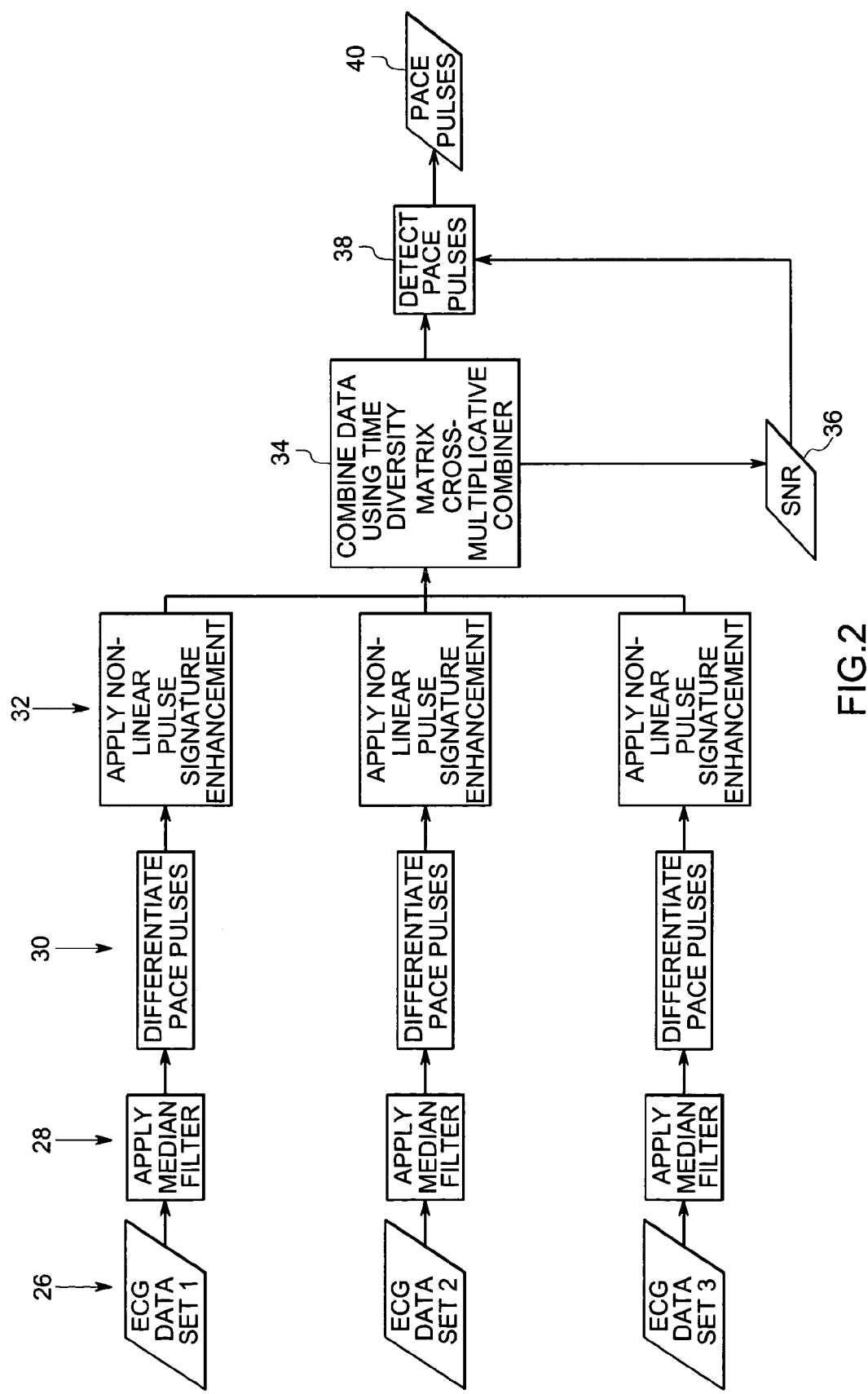
FIG. 2 depicts a flowchart illustrating a method for detecting pace pulses in electrocardiogram data.

Referring now to FIG. 2, a flowchart, depicting steps for detecting pace pulses in ECG data, in accordance with the present technique, is illustrated. In the example depicted by FIG. 2, a set of ECG data 26 is acquired from each respective electrode wire 12, such as may be connected to a respective electrode 11 disposed on a patient. Although FIG. 2 depicts a system that uses 3 ECG data sets, one of ordinary skill in the art will appreciate that the depicted method may be generally applicable to ECG systems employing two or more data sets.

As will be appreciated by one of ordinary skill in the art, in patients having a pacemaker, a programmer may be employed to set the characteristics of the pacemaker, such as, but not limited to, the width and amplitude of the pacemaker pulses. Furthermore, the programmer may generate pulses that may be similar to the pacemaker pulses that may disadvantageously lead to false detection of pace pulses. As a result, for such patients, the ECG data 26 acquired from the respective electrodes 11 may include spurious signals, such as, but not limited to, programmer pulses of short duration associated with pacemakers. Additionally, the acquired ECG data 26 may include overshoots of input pulses. The presence of programmer pulses and overshoots in the ECG data 26 may impede the efficient detection of pace pulses in the ECG data 26.

To address one or more of these problems, the present technique may process the ECG data sets 26 to allow more efficient and accurate detection of pace pulses. For example, in one embodiment of the present technique, each set of ECG data 26 may be filtered to reduce the presence of spurious signals. For example, in step 28, a median filter may be applied to each respective ECG data sets 26. In one embodiment, the median filter may have an order equal to 25. Processing the ECG data 26 via a median filter may attenuate spurious signals related to the presence of programmer pulses. For example, the application of a median filter may result in the rejection of short duration programmer pulses. In addition, by applying the median filter to the ECG data 26, the pace pulses may be "cleaned up," i.e., better defined. For example, for input pulses having an overshoot, the pulses may be squared off, so that the overshoot does not widen the pulses if a differentiation step is subsequently performed. Conversely, input pulses without overshoot, i.e., clean pulses, may pass through the filtering process without modification. Therefore, as a result of the filtering step 28, the ECG data 26 may be relatively free of spurious signals and overshoots after application of a filter, such as a median filter.

The ECG data 26 may also be processed with a differentiator. For example, at step 30, the respective sets of ECG data 26 may be differentiated to convert each pace pulses present within the ECG data 26 into a pair of impulses of opposite polarity. As depicted, the differentiation step 30 may be performed subsequent to a filtration step 28, though this need not be the case. Differentiation may be accomplished via a simple first-order difference equation. In this example, as will be appreciated by one of ordinary skill in the art, if the input signal to the differentiator is represented as x(i), then the output of the differentiator, x'(i) may be represented as:

$$x'(i)=x(i)-x(i-1) \quad (1)$$

As a result of the differentiation process 30, superfluous low-frequency signals present in the ECG data 26 may be reduced or eliminated. For example, in the ECG data 26 that has undergone differentiation at step 30, the QRS complexes may be attenuated and baseline shifts due to respiration may be reduced or eliminated. Furthermore, after attenuation at step 30, extraneous noise, such as 60 Hz noise, in the ECG data 26 may be attenuated.

In addition, in accordance with an exemplary embodiment of the present technique, at step 32, the respective sets of ECG data 26 may be further processed using a variable width non-linear pulse signature enhancer (NLPSE). In general, the input to the variable width NLPSE may be ECG data 26 that may include a pair of impulses of opposite polarity corresponding to each pace pulse, such as may be present after differentiation of the ECG data 26 at step 30. Application of the variable width NLPSE at step 32 may enhance the train of impulses corresponding to the pace pulses and, thereby, relatively attenuate impulsive noise in the ECG data 26. For example, given an input x(i), the output y(i) of an exemplary NLPSE may be represented as:

$$y(i) = \sqrt{\left( \sum_{k=wmin}^{wmax} [|x(i)x(i-k)| - x(i)x(i-k)] - \sum_{j=gate}^{wmin-1} |x(i-j)|^R \right)} \quad (2)$$

where wmin is the minimum pulse width, wmax is the maximum pulse width and gate is the maximum differentiated pulse width. Furthermore, the term $$\sum_{k=wmin}^{wmax} [|x(i)x(i-k)| - x(i)x(i-k)]$$

may be referred to as a negative product accumulation term. The terms |x(i)x(i−k)| and x(i)x(i−k) may represent dual impulse correlator terms. Additionally, the term $|x(i-j)|^R$ may represent the DC rejection term with R representing the weighting factor for this term.

As may be inferred from equation (2), the variable width NLPSE utilizes the bipolar nature of the differentiated ECG data. According to an exemplary embodiment of the present technique, the impulses in the ECG data 26 which are of opposite polarity, such as after differentiation at step 30, may be used to generate an output pulse of large amplitude via operation of the negative product accumulation term. For example, two impulses of opposite polarity, which are separated by a reference distance, w, which may take on values between wmin and wmax, may generate a large amplitude output pulse, in accordance with equation (2). Conversely, if the two impulses are not of opposite polarity or if the two impulses are not separated by the reference distance, w, the negative product accumulation term may be attenuated and no large amplitude output pulse results.

Furthermore, as will be appreciated by one skilled in the art, the width of the pace pulse present in the ECG data 26 may vary. In accordance with equation (2), the variable width NLPSE may be configured to accept a range of pace pulse widths. According to one embodiment of the present technique, a variation of pulse width in the range of 0.22 to 0.64 milliseconds (or 11 to 32 samples for a 50 kHz sampling rate), may be accommodated. Additionally, it may be desirable that the widths of each of the differentiated impulses not exceed 0.1 milliseconds, in order to facilitate the generation of an output pulse of large amplitude.

As may be appreciated by those of ordinary skill in the art, the DC rejection term of equation (2) may represent a penalty term, which will reduce the amplitude of the output if the signal level between the two differentiated pulses is not small. While the preferred value for the weighting factor R is 1.8, other embodiments of the present technique, the value of R may be in the range of 1 to 2. In addition, an absolute value of the DC rejection term, $x(i-j)$, may be considered in order to avert the erroneous weighting of the DC rejection term in equation (2).

As may be appreciated by those of ordinary skill in the art, application of the variable width NLPSE to the ECG data 26, such as the differentiated ECG data, may enable the suppression of impulsive noise. In addition, spurious signals due to slowly varying signals of high-amplitude may be eliminated by application of the variable width NLSPE. Therefore, an output of step 32 may be ECG data, which includes a pulse of large amplitude at the trailing edge of each pace pulse within the ECG data 26. As will be appreciated by one of ordinary skill in the art that the pre-processing module 16 (of FIG. 1) may also function independent of applying the median filter and non-linear pulse signature enhancement to the ECG data.

As may be noted in FIG. 2, the various steps described above are discussed and depicted as being performed on the respective ECG data sets 26 acquired from each respective lead 12 or other source. As depicted at step 34, the respective ECG data sets 26, after some or all of the processes described at steps 28, 30, and 32 have been performed, may be combined at step 34 to generate a combined set of ECG data. For example, the ECG data sets 26 may be combined via a time-diversity matrix cross-multiplicative combiner. As will be appreciated by one skilled in the art, the combiner may be employed when two or more sets of ECG data are available for processing.

As depicted at step 34, the respective ECG data sets 26 may be combined into a single signal. As will be appreciated by one skilled in the art, it may be advantageous to retain the desired signals while attenuating noise during the combining step 34. This may be facilitated in embodiments of the present technique employing a cross-multiplicative combining process since cross multiplying enhances correlated signals, such as pace pulses, while reducing uncorrelated signals, such as noise. In one exemplary embodiment, the combination at step 34 may be as accomplished in accordance with the equation:

$$\sqrt{\left( \sum_{i=0}^{T-1} \sum_{j=0}^{T-1} |x(i-j)y(i-k)| + \sum_{i=0}^{T-1} \sum_{j=0}^{T-1} |x(i-j)z(i-k)| + \sum_{i=0}^{T-1} \sum_{j=0}^{T-1} |y(i-j)z(i-k)| \right)} \quad (3)$$

where $x(i)$, $y(i)$ and $z(i)$ represent the respective ECG data sets 26 in the three lead system depicted in FIG. 2 and T is the time diversity width in samples.

In equation (3), the sum under the radical is a combination of the three individual leads multiplied two at a time. The cross-multiplication takes advantage of the significant correlation between the signal components on the three leads, thereby enhancing the pace signals. The cross-multiplication also beneficially facilitates the attenuation of uncorrelated impulsive noise that may otherwise be mistaken as pace pulses. As will be appreciated, the signals containing the pace pulses from the three individual data sets may have a time lag within the three leads in reaching the combiner. According to an embodiment of the present technique, the combiner allows for the time diversity of the received ECG signals by using a time diversity width T greater than 1. The result of step 34 is a single signal that may include the pace pulses. As will be appreciated by those of ordinary skill in the art, equation (3) may be modified to accommodate different numbers of ECG data sets 26.

Figure 3:
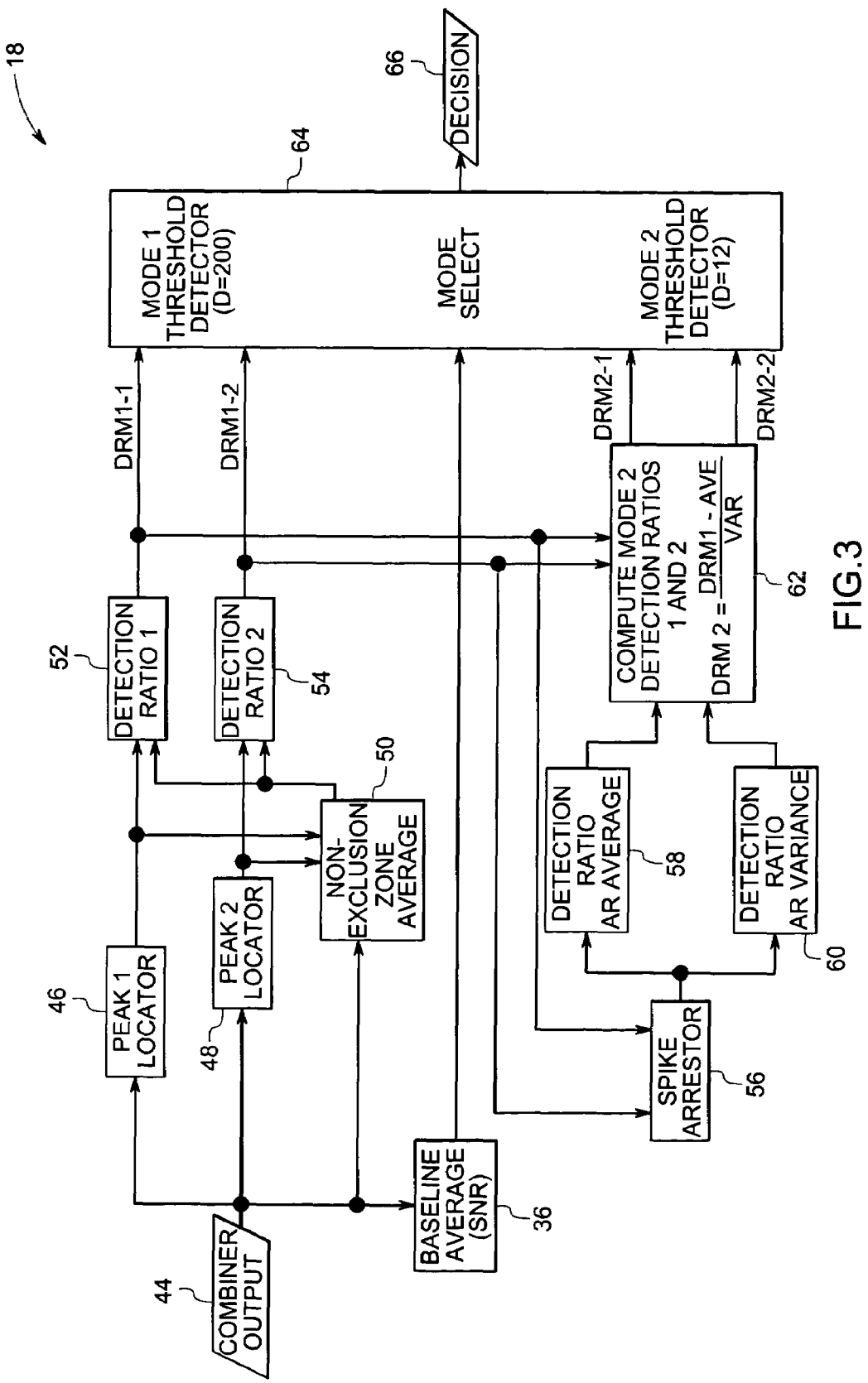
FIG. 3 is a flowchart illustrating the operation of the detector module that facilitates the detection of pace pulses in electrocardiogram data.

Subsequently, a SNR value 36 of the single combined signal may be computed. At step 38, the pace pulses 40 that may be present in the output of the combiner may be detected. Referring now to FIG. 3, a flowchart, depicting steps for detecting pace pulses in ECG data based upon the SNR value 36, in accordance with an exemplary embodiment of the present technique, is illustrated. Alternatively, the detector module may also operate in a simple mode that is independent of the SNR. In the example depicted in FIG. 3, the output 44 of the combiner 34 (of FIG. 2) may serve as an input to the detector module. Also, in the depicted exemplary embodiment, a SNR value 36 of the output 44 of the combiner 34, which may represent a baseline average value, may be computed and used in the detection process. In particular, an algorithm for detecting the pace pulses 40 (of FIG. 2) may be selected based upon the computed SNR value 36.

For example, according to an exemplary embodiment of the present technique, for an SNR value 36 within a normal range, a normal mode of detection of pace pulses 40 may be performed. In this normal mode, the detection of pace pulses 40 may be performed on a frame-by-frame basis, which may be independent of adjacent data. In accordance with an exemplary embodiment of the present technique, a frame may be defined to include 40 milliseconds of ECG data, or 2000 samples at a sampling rate of 50 kHz. For instance, in order to detect biventricular pacing, it may be desirable to locate two pace pulses 40 within each frame. The greater of the two values within a frame, referred to as a first peak value 46, may be selected. An exclusion zone may be set around the first peak value 46 to reduce or eliminate multiple detections of single pulses. For example, in one embodiment, the second peak value 48 is located outside the exclusion zone around the first peak value 46 to prevent such multiple detections of a single pulse. If either peak value 46 or peak value 48 is positioned near the end of the frame, additional input signal may be retrieved and processed, which may prevent the same pace pulse 40 from being detected in the next frame.

Additionally, an average signal level 50 outside the exclusion zone set around the first peak value 46 may be computed. A detection ratio, also referred to as a Mode1 Ratio 52 (DRM1-1), may be computed for the first peak value 46 employing:

$$\text{Mode1 Ratio} = \frac{\text{peak}}{\text{non\_exclusion\_zone average}} \quad (4)$$

where the detection ratio may be measured over a 2,000 sample frame.

If the Mode1 Ratio 52 for the first peak value 46, that is, the ratio of the peak level to the average level exceeds a predetermined threshold, a first pace pulse 40 may be detected. The threshold detector 64 may be employed to facilitate the comparison of the Mode1 Ratio with the pre-determined threshold value. According to one embodiment of the present technique, a threshold value equivalent to 200, as empirically determined, may be selected. Similarly, a Mode1 Ratio 54 (DRM1-2) may be computed for the second peak value 48 using equation (4). If the Mode1 Ratio 54 for the second peak value 48 exceeds the pre-determined threshold value, a second pace pulse 40 may be detected. The decision 66 represents the detection of pace pulses 40.

Alternatively, if the SNR of the input signal is significantly low, as may be determined in one embodiment when the autoregressive average of baseline signal exceeds a threshold value equivalent to 2, a second mode of detection of pace pulses 40 may be employed. The second mode of detection of pace pulses 40 may, in one embodiment, be accomplished via autoregressive averaging of detection ratios of previous frames. An autoregressive estimate of an inter-frame average 58 of the Mode1 Ratios may be computed as:

$$AVE = 0.7*AVE + 0.3*Mode1Ratio \quad (5)$$

where the Mode1 Ratio may be represented by equation (4).

Similarly, an autoregressive estimate of a variation 60 of the Mode1 Ratios may be computed as:

$$VAR = 0.8*VAR + 0.2*|Mode1Ratio - AVE| \quad (6)$$

As illustrated in FIG. 3, a spike arrestor may be employed to prevent actual pace pulses from being included in the AVE and VAR computations in equations (5) and (6). In the preferred embodiment, any Mode1Ratio greater than 20 times the current value of AVE will not be used to update the estimates.

A ratio, also referred to as a Mode2 Ratio (DRM2-1) 62, may be computed employing the Mode1 Ratio of equation (4), the autoregressive estimate of an inter-frame average of equation (5), and the variance of the Mode1 Ratio of equation (6) corresponding to the first peak value 46. For example, the Mode2 Ratio (DRM2-1) 62 may be evaluated as:

$$\text{Mode2 Ratio} = \frac{(\text{Mode1 Ratio} - AVE)}{VAR} \quad (7)$$

Similarly, a Mode2 Ratio 62 (DRM2-2) may be computed for the second peak value 48 using equation (7). As described above with reference to the normal mode of operation of the detector module, the Mode2 Ratios DRM2-1, DRM2-2 may be compared against a pre-determined threshold value via the threshold detector 64. In accordance with one aspect of the present technique, a threshold value equivalent to 12 may be employed. If the value of Mode2 Ratios 62 exceeds the threshold value, a pace pulse 40 may be detected.

Once detected, by either the normal or the low SNR techniques described herein, the pace pulses 40 may be exhibited on a display unit, such as a printer 24 (of FIG. 1) or a display 22 (of FIG. 1) for review by a doctor or other medical professional. For example, the pace pulses 40 may be superimposed on an ECG trace displayed on a display 22 or a printout generated by printer 24. Alternatively, the pace pulses 40 may be displayed as a second trace coinciding in time with an ECG trace.

As will be appreciated by those of ordinary skill in the art, the foregoing example, demonstrations, and process steps may be implemented by suitable code on a processor-based system, such as a general-purpose or special-purpose computer. It should also be noted that different implementations of the present technique may perform some or all of the steps described herein in different orders or substantially concurrently, that is, in parallel. Furthermore, the functions may be implemented in a variety of programming languages, such as C++ or JAVA. Such code, as will be appreciated by those of ordinary skill in the art, may be stored or adapted for storage on one or more tangible, machine readable media, such as on memory chips, local or remote hard disks, optical disks (that is, CD's or DVD's), or other media, which may be accessed by a processor-based system to execute the stored code. Note that the tangible media may comprise paper or another suitable medium upon which the instructions are printed. For instance, the instructions can be electronically captured via optical scanning of the paper or other medium, then compiled, interpreted or otherwise processed in a suitable manner if necessary, and then stored in a computer memory.

While only certain features of the invention have been illustrated and described herein, many modifications and changes will occur to those skilled in the art. In particular, though the present examples and discussions are directed to the detection of pacemaker pulses, one of ordinary skill in the art will appreciate that, the present techniques may be used in the general detection of rectangular pulses. It is, therefore, to be understood that the appended claims are intended to cover all such modifications and changes as fall within the true spirit of the invention.

The invention claimed is:

1. A method for detecting pace pulses, the method comprising the steps of:
   processing one or more sets of digital electrocardiogram data via a non-linear enhancement algorithm;
   detecting one or more pulses in the one or more sets of digital electrocardiogram data via a non-linear detection algorithm; and
   displaying the pace pulses on a display unit.

2. The method of claim 1, wherein processing one or more sets of digital electrocardiogram data comprises filtering the one or more sets of electrocardiogram data.

3. The method of claim 2, wherein filtering the one or more sets of digital electrocardiogram data comprises applying a median filter.

4. The method of claim 1, wherein processing one or more sets of digital electrocardiogram data comprises applying a non-linear pulse signature enhancement to the one or more sets of digital electrocardiogram data.

5. The method of claim 4, comprising processing the one or more sets of digital electrocardiogram data with a differentiator.

6. The method of claim 4, wherein applying the non-linear pulse signature enhancement comprises enhancing a pulse signature of differentiated pace pulses.

7. The method of claim 1, comprising the step of acquiring at least one respective set of electrocardiogram data from at least one electrode.

8. The method of claim 7, comprising the step of digitizing the each set of electrocardiogram data to generate each set of digitized electrocardiogram data.

9. The method of claim 1, comprising the step of combining two or more sets of digital electrocardiogram data via a cross-multiplicative combiner to generate a combined set of digital electrocardiogram data.

10. The method of claim 1, wherein detecting one or more pulses in the one or more sets of digital electrocardiogram data comprises detecting one or more pace pulses in the one or more sets of electrocardiogram data based upon a signal to noise ratio.

11. The method of claim 10, wherein detecting one or more pulses in the one or more sets of digital electrocardiogram data based upon a signal to noise ratio comprises detecting a signal to noise ratio associated with the combined set of electrocardiogram data.

12. The method of claim 1, wherein displaying the pace pulses comprises superimposing the pace pulses on an electrocardiogram trace.

13. A computer program comprising one or more tangible media, wherein the one or more tangible media comprise:
  code adapted to process one or more sets of digital electrocardiogram data via a non-linear enhancement algorithm;
  code adapted to detect one or more pulses in the one or more sets of digital electrocardiogram data via a non-linear detection algorithm; and
  code adapted to display the pace pulses on a display unit.

14. The computer program, as recited in claim 13, wherein the code adapted to process one or more sets of digital electrocardiogram data comprises:
  code adapted to filter one or more sets of electrocardiogram data;
  code adapted to process the one or more sets of electrocardiogram data with a differentiator;
  code adapted to apply a non-linear pulse signature enhancement to the one or more sets of electrocardiogram data; and
  code adapted to combine two or more sets of electrocardiogram data via a cross-multiplicative combiner to generate a combined set of electrocardiogram data.

15. The computer program, as recited in claim 14, wherein the code adapted to filter the one or more sets of electrocardiogram data applies a median filter.

16. The computer program, as recited in claim 14, wherein the code is adapted to detect one or more pace pulses in the combined set of electrocardiogram data.

17. The computer program, as recited in claim 16, wherein the code adapted to detect pace pulses in the combined electrocardiogram data is adapted to detect pace pulses based upon a signal to noise ratio.

18. An electrocardiogram system, the system comprising:
  a pre-processor module configured to filter one or more sets of electrocardiogram data, to apply a non-linear pulse signature enhancement to the one or more sets of electrocardiogram data, and to combine two or more sets of electrocardiogram data via a cross-multiplicative combiner to generate a combined set of electrocardiogram data; and
  a detector module configured to detect pace pulses in the combined set of electrocardiogram data.

19. The electrocardiogram system of claim 18, comprising an acquisition module configured to acquire one or more sets of electrocardiogram data.

20. The electrocardiogram system of claim 19, comprising at least one electrode configured to provide the electrocardiogram data to the acquisition module.

21. The electrocardiogram system of claim 19, wherein the acquisition module is further configured to digitize the one or more sets of electrocardiogram data.

22. The electrocardiogram system of claim 18, comprising an operator console configured to display the pace pulses.

23. The electrocardiogram system of claim 22, wherein the operator console is configured to display the pace pulses superimposed on an electrocardiogram trace.

24. The electrocardiogram system of claim 22, wherein the operator console is configured to display the pace pulses on at least one of a printer and a display unit.

25. The electrocardiogram system of claim 18, wherein the pre-processing module is configured to filter the one or more sets of electrocardiogram data by applying a median filter.

26. The electrocardiogram system of claim 18, wherein the pre-processing module is configured to process the one or more sets of electrocardiogram data with a differentiator.

27. The electrocardiogram system of claim 18, comprising a cross-multiplicative combiner configured to combine two or more sets of electrocardiogram data to generate a combined set of electrocardiogram data.

28. The electrocardiogram system of claim 27, wherein the detector module is configured to detect one or more pace pulses in the combined set of electrocardiogram data based upon a signal to noise ratio.

29. An electrocardiogram system, the system comprising:
  means for processing one or more sets of digital electrocardiogram data via a non-linear enhancement algorithm;
  means for detecting one or more pulses in the one or more sets of digital electrocardiogram data via a non-linear detection algorithm; and
  means for displaying the one or more pulses on a display unit.

30. A method for detecting a pace pulse, the method comprising:
  processing two or more sets of electrocardiogram data with a differentiator;
  applying a non-linear pulse signature enhancement to the two or more sets of electrocardiogram data; and
  combining the two or more sets of electrocardiogram data via a cross-multiplicative combiner to generate a combined set of electrocardiogram data.

31. The method of claim 30, wherein applying the non-linear pulse signature enhancement enhances the differentiated electrocardiogram data by suppressing impulsive noise.

32. The method of claim 30, comprising acquiring the two or more sets of electrocardiogram data.

33. The method of claim 30, comprising processing the two or more sets of electrocardiogram data with a filter.

34. The method of claim 30, comprising detecting one or more pace pulses in the combined electrocardiogram data.

35. The method of claim 34, comprising displaying the pace pulses on a display unit.

36. An electrocardiogram system, the system comprising:
  a first processing module configured to process two or more sets of electrocardiogram data with a differentiator;
  a second processing module configured to apply non-linear pulse signature enhancement to the two or more sets of electrocardiogram data; and
  a cross-multiplicative combiner configured to combine two or more sets of electrocardiogram data to generate a combined set of electrocardiogram data.

37. The electrocardiogram system of claim 36, comprising an acquisition module configured to acquire the two or more sets of electrocardiogram data.

38. The electrocardiogram system of claim 36, comprising a module configured to filter the two or more sets of electrocardiogram data.

39. The electrocardiogram system of claim 36, comprising a detector module configured to detect one or more pace pulses in the combined set of electrocardiogram data.

40. The electrocardiogram system of claim 39, comprising an operator console configured to display the pace pulses.

41. A computer program comprising one or more tangible media, wherein the one or more tangible media comprise:

code adapted to process one or more sets of electrocardiogram data with a differentiator; and
code adapted to apply a non-linear pulse signature enhancement to one or more sets of electrocardiogram data.

42. The computer program, as recited in claim 41, comprises:
code adapted to acquire one or more sets of electrocardiogram data;
code adapted to filter the one or more sets of electrocardiogram data;
code adapted to combine via a cross-multiplicative combine two or more sets of electrocardiogram data to generate a combined set of electrocardiogram data; and
code adapted to detect one or more pace pulses in combined set of electrocardiogram data.

43. An electrocardiogram system, the system comprising:
means for processing the one or more sets of electrocardiogram data with a differentiator;
means for applying a non-linear pulse signature enhancement to the one or more sets of electrocardiogram data; and
means for displaying the pulse on a display unit.

44. A method for detecting a pace pulse, the method comprising:
detecting a signal to noise ratio;
detecting the pace pulse based upon the signal to noise, wherein detecting the pace pulse comprises applying a detection algorithm corresponding to the signal to noise ratio level; and
displaying the place pulse on a display unit.

45. The method of claim 44, wherein the signal to noise ratio corresponds to one level of two or more levels of signal to noise ratio.

46. The method of claim 44, comprising acquiring one or more sets of electrocardiogram data.

47. The method of claim 44, comprising processing the one or more sets of electrocardiogram data with a filter.

48. The method of claim 44, comprising processing the one or more sets of electrocardiogram data with a differentiator.

49. The method of claim 44, comprising applying a non-linear pulse signature enhancement to the one or more sets of electrocardiogram data.

50. The method of claim 44, comprising combining two or more sets of electrocardiogram data via a cross-multiplicative combiner to generate a combined set of electrocardiogram data.

51. An electrocardiogram system, the system comprising:
a detection module configured to detect a pace pulse based upon a signal to noise ratio, wherein detecting the pace pulse comprises applying a detection algorithm corresponding to the signal to noise ratio level; and
an operator console configured to display the pace pulses.

52. The electrocardiogram system of claim 51, comprising an acquisition module configured to acquire one or more sets of electrocardiogram data.

53. The electrocardiogram system of claim 51, comprising a module configured to filter one or more sets of electrocardiogram data.

54. The electrocardiogram system of claim 51 comprising a module configured to process the one or more sets of electrocardiogram data with a differentiator.

55. The electrocardiogram system of claim 51, comprising a module configured to apply a non-linear pulse signature enhancement to the one or more sets of electrocardiogram data.

56. The electrocardiogram system of claim 51, comprising a cross-multiplicative combiner configured to combine two or more sets of electrocardiogram data to generate a combined set of electrocardiogram data.

57. A computer program comprising one or more tangible media, wherein the one or more tangible media comprise:
code adapted to detecting a signal to noise ratio; and
code adapted to detect a pace pulse based upon the signal to noise, wherein code adapted to detect a pace pulse comprises code adapted to apply a detection algorithm corresponding to the signal to noise ratio level; and
code adapted to display the pace pulse on a display unit.

58. The computer program, as recited in claim 57, comprises:
code adapted to acquire one or more sets of electrocardiogram data;
code adapted to filter the one or more sets of electrocardiogram data;
code adapted to process the one or more sets of electrocardiogram data via a differentiator;
code adapted to apply a non-linear pulse signature enhancement to the one or more sets of electrocardiogram data; and
code adapted to combine via a cross-multiplicative combine two or more sets of electrocardiogram data to generate a combined set of electrocardiogram data.

59. An electrocardiogram system, the system comprising:
means for detecting a signal to noise ratio; and
means for detecting a pace pulse based upon the signal to noise, wherein means for detecting a pace pulse comprises applying a detection algorithm corresponding to the signal to noise ratio level; and
means for displaying the pace pulse on a display unit.

60. A method for combining a two or more sets of electrocardiogram data, the method comprising:
combining the two or more sets of electrocardiogram data via a cross-multiplicative combiner to generate a combined set of electrocardiogram data;
detecting one or more pace pulses in the combined set of electrocardiogram data.

61. The method of claim 60, wherein combining the plurality of sets of electrocardiogram data comprises enhancing one or more pace pulses and attenuating impulsive noise.

62. The method of claim 60, comprising acquiring one or more sets of electrocardiogram data.

63. The method of claim 60, comprising processing the one or more sets of electrocardiogram data with a filter.

64. The method of claim 60, comprising processing the one or more sets of electrocardiogram data with a differentiator.

65. The method of claim 60, comprising applying a non-linear pulse signature enhancement to the one or more sets of electrocardiogram data.

66. The method of claim 60, comprising displaying the pace pulses.

67. An electrocardiogram system, the system comprising:
a cross-multiplicative combiner configured to combine two or more sets of electrocardiogram data to generate a combined set of electrocardiogram data; and
a detector module configured to detect one or more pace pulses in the combined set of electrocardiogram data.

68. The electrocardiogram system of claim 67, comprising an acquisition module configured to acquire one or more sets of electrocardiogram data.

69. The electrocardiogram system of claim 67, comprising a module configured to filter one or more sets of electrocardiogram data.

70. The electrocardiogram system of claim 67, comprising a module configured to process one or more sets of electrocardiogram data with a differentiator.

71. The electrocardiogram system of claim 67, comprising a module configured to apply a non-linear pulse signature enhancer to the one or more sets of electrocardiogram data.

72. The electrocardiogram system of claim 67, comprising an operator console configured to display the pace pulses.

73. A computer program comprising one or more tangible media, wherein the one or more tangible media comprise:
   code adapted to combine two or more sets of electrocardiogram data via a cross-multiplicative combiner to generate a combined set of electrocardiogram data; and
   code adapted to detect one or more pace pulses in combined set of electrocardiogram data.

74. The computer program, as recited in claim 73, comprises:
   code adapted to acquire one or more sets of electrocardiogram data;
   code adapted to filter the one or more sets of electrocardiogram data;
   code adapted to process the one or more sets of electrocardiogram data via a differentiator; and
   code adapted to apply a non-linear pulse signature enhancement to the one or more sets of electrocardiogram data.

75. An electrocardiogram system, the system comprising:
   means for combining two or more sets of electrocardiogram data via a cross-multiplicative combiner to generate a combined set of electrocardiogram data; and
   means for detecting one or more pace pulses in the combined set of electrocardiogram data.

* * * * *

UNITED STATES PATENT AND TRADEMARK OFFICE
CERTIFICATE OF CORRECTION

PATENT NO.        : 7,471,977 B2
APPLICATION NO.   : 10/881865
DATED             : December 30, 2008
INVENTOR(S)       : Zinser, Jr. et al.

Page 1 of 1

It is certified that error appears in the above-identified patent and that said Letters Patent is hereby corrected as shown below:

In Column 11, Line 31, in Claim 44, delete "place" and insert -- pace --, therefor.

Signed and Sealed this

Seventh Day of July, 2009

JOHN DOLL
*Acting Director of the United States Patent and Trademark Office*